(12) United States Patent
Bartels et al.

(10) Patent No.: US 9,283,081 B2
(45) Date of Patent: Mar. 15, 2016

(54) JOINT PROSTHESIS HAVING A BENDING HINGE THAT COMPRISES A SPREADING AXLE

(75) Inventors: Carolin Bartels, Barmstedt (DE); Klaus Dmuschewsky, Hamburg (DE); Marco Iredi, Norderstedt (DE)

(73) Assignee: Waldemar Link GmbH & Co. KG, Hamburg (DE)

( * ) Notice: Subject to any disclaimer, the term of this patent is extended or adjusted under 35 U.S.C. 154(b) by 0 days.

(21) Appl. No.: 14/112,812

(22) PCT Filed: Apr. 19, 2012

(86) PCT No.: PCT/EP2012/057165
§ 371 (c)(1),
(2), (4) Date: Oct. 18, 2013

(87) PCT Pub. No.: WO2012/143445
PCT Pub. Date: Oct. 26, 2012

(65) Prior Publication Data
US 2014/0039635 A1    Feb. 6, 2014

(30) Foreign Application Priority Data

Apr. 20, 2011  (EP) .................................... 11163204

(51) Int. Cl.
*A61F 2/30* (2006.01)
*A61F 2/38* (2006.01)

(52) U.S. Cl.
CPC .................. *A61F 2/384* (2013.01); *A61F 2/385* (2013.01); *A61F 2002/30187* (2013.01);
(Continued)

(58) Field of Classification Search
CPC ............ A61F 2002/30187; A61F 2002/30505; A61F 2002/30504; A61F 2/385; A61F 2/38; A61F 2/3804; A61F 2/384; A61F 2002/3809; A61F 2002/3813; A61F 2002/3818; A61F 2002/3822; A61F 2002/3827; A61F 2002/3831; A61F 2/40; A61F 2/42
USPC ........... 623/20.12, 20.24, 20.14, 20.26, 20.27
See application file for complete search history.

(56) References Cited

U.S. PATENT DOCUMENTS 2,696,817 A * 12/1954 Prevo .......................... 623/20.12
3,934,272 A *  1/1976 Wearne et al. ............. 623/20.26
(Continued)

FOREIGN PATENT DOCUMENTS

| DE | 2 122 390 | 1/1973 |
| EP | 1 381 335 | 1/2004 |
| FR | 2 793 677 | 11/2000 |

OTHER PUBLICATIONS

International Search Report and Written Opinion mailed Jun. 4, 2012, directed to International Application No. PCT/EP2012/057165; 16 pages.

*Primary Examiner* — Alvin Stewart
(74) *Attorney, Agent, or Firm* — Morrison & Foerster LLP

(57) ABSTRACT

A joint prosthesis has a bending hinge, which is formed by a hinge fork and an axle pin, which comprises two axle stubs, which are arranged in an installation position for insertion, in which installation position the axle stubs are retracted in a coupling piece, and in an expanded position after implantation by movement in the axial direction into aligned hinge holes of the hinge fork, wherein the axle pin has two bearing areas at the ends of the axle pin and a joining area lying therebetween, and the axle pin is separated in the joining area along a plane extending in the axial direction, which plane intersects with the jacket of the axle pin at two points.

18 Claims, 4 Drawing Sheets

(52) U.S. Cl.
CPC ............... *A61F 2002/30373* (2013.01); *A61F 2002/30484* (2013.01); *A61F 2002/30505* (2013.01); *A61F 2002/30509* (2013.01); *A61F 2002/30565* (2013.01)

(56) References Cited

U.S. PATENT DOCUMENTS

| | | | |
|---|---|---|---|
| 3,990,117 A * | 11/1976 | Pritchard et al. | 623/20.12 |
| 4,262,368 A * | 4/1981 | Lacey | 623/20.25 |
| 5,314,481 A * | 5/1994 | Bianco | 623/20.25 |
| 5,370,701 A * | 12/1994 | Finn | 623/20.25 |
| 5,954,770 A * | 9/1999 | Schmotzer et al. | 623/20.24 |
| 6,290,725 B1 * | 9/2001 | Weiss et al. | 623/20.12 |
| 6,984,249 B2 * | 1/2006 | Keller | 623/20.24 |
| 7,572,292 B2 * | 8/2009 | Crabtree et al. | 623/20.24 |
| 7,918,893 B2 * | 4/2011 | Romeis et al. | 623/20.24 |
| RE42,805 E * | 10/2011 | Tornier et al. | 623/20.12 |
| 8,268,006 B2 * | 9/2012 | Meyers et al. | 623/20.29 |
| 8,545,570 B2 * | 10/2013 | Crabtree et al. | 623/20.24 |
| 8,613,774 B2 * | 12/2013 | Bartel et al. | 623/20.12 |
| 8,932,362 B2 * | 1/2015 | Katrana et al. | 623/20.11 |
| 2004/0186584 A1 * | 9/2004 | Keller | 623/20.24 |
| 2004/0243243 A1 * | 12/2004 | Tornier | 623/20.12 |
| 2005/0107886 A1 * | 5/2005 | Crabtree et al. | 623/20.24 |
| 2008/0167722 A1 * | 7/2008 | Metzger et al. | 623/20.36 |
| 2009/0024221 A1 * | 1/2009 | Ball | 623/20.11 |
| 2009/0149964 A1 * | 6/2009 | May et al. | 623/20.15 |
| 2010/0174378 A1 * | 7/2010 | Metzger et al. | 623/20.28 |
| 2010/0179661 A1 * | 7/2010 | Berelsman et al. | 623/20.12 |
| 2012/0221113 A1 * | 8/2012 | Katrana et al. | 623/20.12 |
| 2014/0025174 A1 * | 1/2014 | Lucas et al. | 623/20.24 |
| 2014/0039635 A1 * | 2/2014 | Bartels et al. | 623/20.24 |
| 2014/0148913 A1 * | 5/2014 | Bartels et al. | 623/23.41 |
| 2014/0236307 A1 * | 8/2014 | Whiteside | 623/20.26 |
| 2014/0277525 A1 * | 9/2014 | Winslow | 623/20.12 |

* cited by examiner

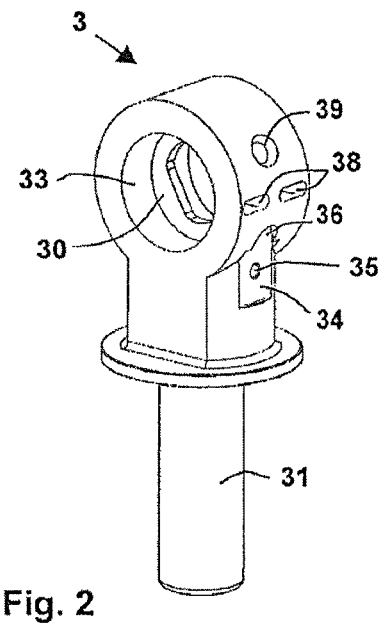
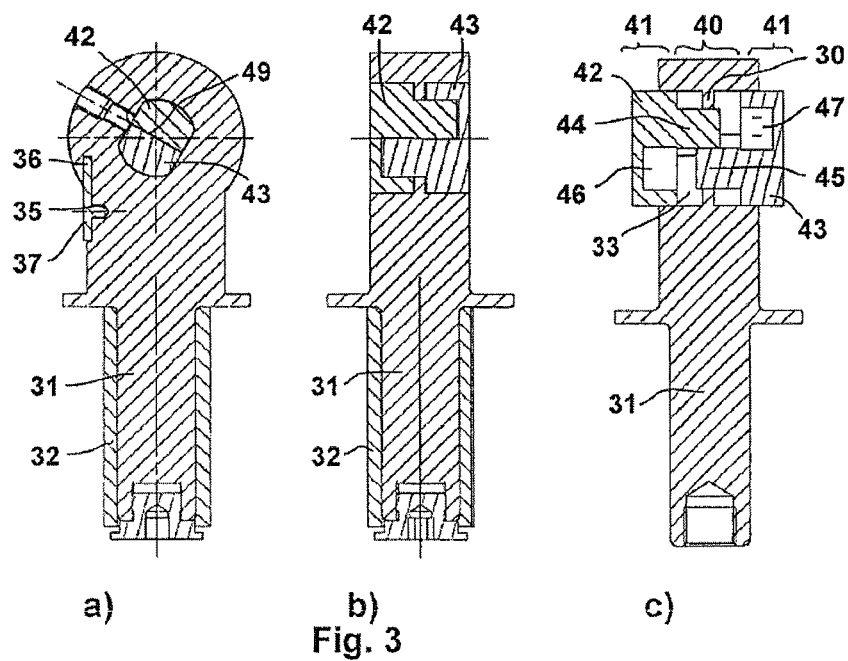
Fig. 2
a)   b)   c)
Fig. 3

JOINT PROSTHESIS HAVING A BENDING HINGE THAT COMPRISES A SPREADING AXLE

REFERENCE TO RELATED APPLICATIONS

This application is a national stage application under 35 USC 371 of International Application No. PCT/EP2012/057165, filed Apr. 19, 2012, which claims the priority of European Application No. 11 163 204.8, filed Apr. 20, 2011, the entire contents of which are incorporated herein by reference.

FIELD OF THE INVENTION

The invention relates to a joint endoprosthesis having a bending hinge, the axial pin of said bending hinge comprising two pin stubs which are arranged in an installation position, in which they are retracted into the coupling piece, for insertion, and are arranged in a spread position after insertion of the central part by being moved in their longitudinal direction into aligned hinge holes in the hinge fork.

BACKGROUND OF THE INVENTION

Endoprostheses of this kind are used, in particular, as prostheses for knee joints. Owing to the high loading on knee joints by virtue of the body weight of the patient and owing to the complex movement sequence of said knee joints, they are comparatively more susceptible to dysfunction due to wear or disease. The replacement of a knee joint by an endoprosthesis is a complicated operation which puts stress on the patient. It is therefore desirable to be able to implant the endoprosthesis in a manner which is as straightforward and insusceptible to faults as possible in order to avoid complications.

To this end, a joint endoprosthesis of the kind cited in the introductory part which has a spreadable axial pin has been disclosed (EP 1 381 335 B1). Said joint endoprosthesis comprises a tibial component and a femoral component which are connected to one another in an articulated manner by means of a coupling piece. A bending joint and a rotary joint are formed. The bending joint allows flexion and extension of the knee. To this end, the coupling piece has an axial eye into which an axial pin, which comprises pin stubs, is inserted. The pin stubs are provided with mutually complementary coaxial recesses, with the result that they can be moved toward one another or away from one another in a telescopic manner along their common center axis. For insertion purposes, the pin stubs have to be moved completely toward one another and are therefore located in an installation position in which the pin stubs are retracted into the coupling piece. After the coupling piece has been installed in the mating piece, a hinge fork on the femoral component, said pin stubs are spread and thereby expand into the holes in the hinge fork which are aligned with one another. As a result, the coupling piece is connected to the femoral component in a pivotable manner. This axial pin allows simpler installation, however complications may arise in the event of the pin stubs becoming jammed.

SUMMARY OF THE INVENTION

The invention is based on the object of providing, proceeding from the last-mentioned prior art, an improved joint endoprosthesis which avoids this disadvantage.

A solution according to the invention can be found as broadly described herein. Advantageous developments are the subject matter of the detailed embodiments described below.

In a joint prosthesis having a bending hinge which is formed by a hinge fork and an axial pin which comprises two pin stubs which are arranged in an installation position, in which they are retracted in a coupling piece, for insertion purposes, and are arranged in an expanded position after implantation by being moved in the axial direction into aligned hinge holes in the hinge fork, provision is made, according to the invention, for the axial pin to have two bearing regions at its ends and a joining region which is situated between said bearing regions, and for the axial pin to be separated in the joining region along a plane which runs in the axial direction and which intersects the casing of the axial pin at two points.

The invention is based on the idea of dividing the joining region of the two pin stubs into two half-shafts, specifically by means of a plane which runs along the center axis and intersects the casing of the axial pin at two points. This is generally, but not necessarily, the center plane. Said plane can be composed of several component planes, but it is continuous in most cases. Since said plane runs from one side to the other side, it has a maximum width, that is to say is the same size as the diameter of the pin in the joining region. This produces a plane which extends over the entire diameter and along which the two pin stubs are guided with their maximum width. Guidance over a wide region ensures favorable friction conditions and thereby prevents jamming. Since, moreover, the guide plane intersects the casing at at least two points, a degree of freedom is available for compensating for tilting. This constitutes a considerable advantage over the prior art with closed—for example hollow-cylindrical—guide planes which can have a tendency to become blocked on account of tilting. The invention therefore provides considerable advantages both during the initial implantation and also in the case of any subsequent adjustments.

The pin stubs preferably complement one another in their joining region. As a result, the same outer contour as that exhibited by the undivided axial pins which are conventionally used can be achieved by simply plug-connecting said pin stubs. The axial pin according to the invention can therefore be used in conventional coupling pieces. Particular preference is given to the pin stubs not only being complementary but even having the same shape. In a well-established embodiment, the pin stubs have half-pegs in the joining region. By way of example, the cross section in the joining region has a half-moon shape.

The coupling piece advantageously has a separating element with an aperture for receiving the joining region of the pin stubs, with the aperture being non-round. As a result, the two pin stubs can be prevented from rotating in the coupling piece. Therefore, a separate rotation-prevention means, for example in the form of a screw which can be easily lost, is no longer required.

A movement-prevention means can be arranged on the coupling piece. Said movement-prevention means acts on the two pin stubs and secures them in their spread position. Therefore, a spring, as provided in the prior art for spreading purposes, is not required. In the event of an adjustment, the pin stubs can therefore be moved into the non-spread installation position by simply removing the movement-prevention means, without it being necessary to permanently overcome the counteracting force of the spreading spring for this purpose.

In order to be able to act on the pin stubs in the coupling piece, an access slot is provided on each coupling piece, preferably for each pin stub. Said access slot is oriented such that its elongate extent lies in the axial direction and has an extent which is at least the same size as the area over which the pin stubs are to be spread. A spreading instrument which can be inserted into the access slots is provided for the purpose of moving the pin stubs. Said spreading instrument is expediently in the form of a clip with two free ends for insertion into the access slots, wherein the free ends can preferably be at an angle of 30 degrees to 75 degrees in relation to one another. Said spreading instrument can be formed from a piece of wire, the wire forming a three-point loop, which faces away from the free ends, in the rear region of said piece of wire. A sliding sleeve can be mounted on said three-point loop, said sliding sleeve moving from an inoperative position, in which the free ends are close to one another, the to a movable spreading position in which the free ends are moved away from one another.

A fastening guide can be arranged on the spreading instrument. Said fastening guide is designed as a sleeve in which a locking screw is arranged. To this end, said sleeve expediently has an internal thread into which the locking screw can be screwed. The fastening guide is oriented such that it targets the pin when the spreading instrument is mounted on the coupling piece. The length of the locking screw is preferably greater than the distance between the coupling-piece-side end of the fastening guide and the joining region of the pin stubs. This ensures that the spreading instrument, together with the fastening guide, can be removed only if the pin stubs are secured in their spread position.

The sliding sleeve can have a circumferential radial collar which has a recess in its side which faces the fastening guide. This ensures movement also on a curved clip of the spreading instrument and a straight access path for a screwdriver to the locking screw which is arranged in the fastening guide.

Furthermore, a pair of adjustment pliers can be provided. Said pair of adjustment pliers has handles at its rear end and receiving fingers at its front end, said receiving fingers being designed to be passed through the access slots and having an oval cross section. The receiving fingers diverge at the front at an angle of preferably between 5 and 25 degrees.

BRIEF DESCRIPTION OF THE DRAWINGS

The invention will be explained in greater detail below with reference to the appended drawing which illustrates an advantageous exemplary embodiment. In said drawing:

FIG. 2 shows a perspective view of the coupling piece;
FIGS. 3a-c show side views of the coupling piece;
FIGS. 4a-c show views of a detail of a pin stub.

DETAILED DESCRIPTION OF THE INVENTION

Figure 1:
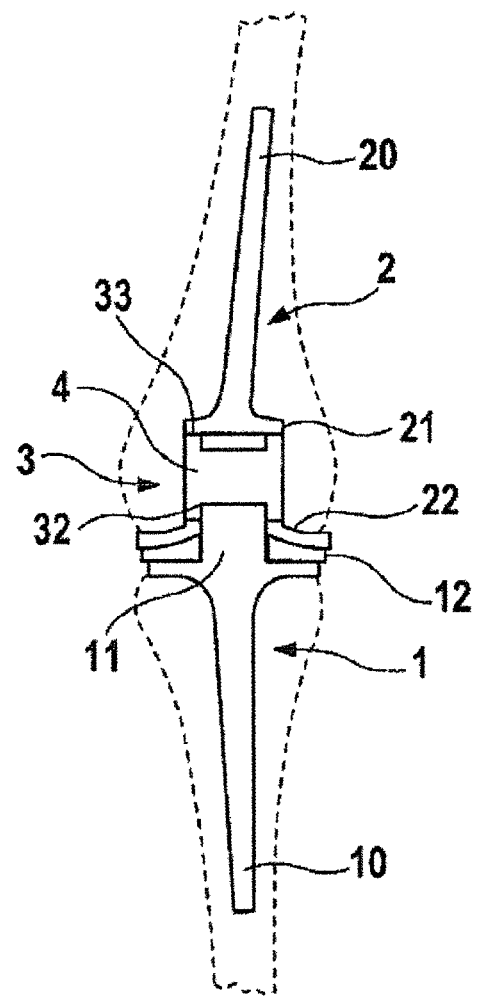
FIG. 1 shows a rear view of a joint prosthesis.

The endoprosthesis according to an exemplary embodiment of the invention will be explained using a knee joint endoprosthesis. The endoprosthesis of a knee joint substantially comprises two components 1, 2, one being in the form of a tibial component 1 and the other being in the form of a femoral component 2. In the femoral component 2, a femoral bearing half 21, which has two condyle-like runners 22 which project in the manner of a fork in relation to the tibial component 1, adjoins a stem 20 which is inserted into a femur of a patient. Said runners are supported on a tibial plateau 12 which is arranged on a tibial bearing half 11 which is fastened to a tibia of the patient by means of a stem 10.

A coupling piece 3 is arranged between said stems, said coupling piece a T-shaped piece 30 as a main body with a receiving eye 33, which is arranged in its upper region, for an axial pin 4 and with a bearing pin 31 for being received in a bearing bushing in the tibial bearing half 11.

A first bearing (flexion bearing) allows a pivoting movement between the components 1 and 2, that is to say realizes the bending movement between the thigh and the lower leg. This pivoting movement about the axis of the axial pin 4 therefore forms the first axis for the movement of the knee joint prosthesis. The pin 31 is oriented transverse to said first axis by way of its center axis which forms a second axis for the rotary movement with which the femur part 2 rotates about the second axis relative to the tibia component 1. For this rotary bearing, the pin 31 of the coupling piece 3 projects into the bearing bushing. A bearing insert 32 is arranged between said pin and bearing bushing.

The spreadable axial pin 4 is arranged in the receiving eye 33. Said axial pin has a plurality of regions, in each case a bearing region 41 at the two ends and a joining region 40 between said two ends. In FIG. 3b, said axial pin is illustrated in its installation position in which it is retracted into the receiving eye 33, and in FIG. 3c is illustrated in its spread position in which the bearing regions 41 project out of the receiving eye 33 on both sides. Said axial pin is passed through an aperture in a separating element 30 in the receiving eye 33, said aperture having the shape of a flattened oval and preventing rotation of the axial pin 4.

The coupling piece 3 is provided with a flat receiving area 35 on its front side (on the left-hand side in the illustration in FIG. 3a). A pocket 36 is formed in the receiving eye 33 at the upper end of said receiving area, said pocket merging with the receiving area 34 in a flat manner at its base. A retaining opening 35 which is designed in the form of a blind hole is provided in the central region of the receiving area 34. An impact-protection plate 37 can be mounted on the receiving area 34 and is inserted into the pocket 36. As a result, the pocket 36 is secured against lifting off from the receiving area 34 by way of its upper edge, specifically also under the action of force from the front (from the left-hand side in FIG. 3a) when the extended stop position of the flexion bearing is reached. The impact-protection plate 37 is protected against movement, in particular in the downward direction, by means of a projection which is formed on the rear face of said impact protection plate and engages in the retaining opening 35 in an interlocking manner.

The axial pin 4 has a separating plane 49, which runs along to form its center axis, in the joining region 40. Said separate plane intersects the casing in the joining region 40 at two diametrically opposite points (see FIG. 3a). The axial pin 4 is thereby divided into two pin stubs 42, 43. The two said pin stubs have a projecting half-peg 44, 45, which pegs form the cross section of the axial pin 4 in the joining region 40 when combined.

Furthermore, each of the two pin stubs 42, 43 has a cavity 46, 47 in the shape of a half moon. Said cavities are shaped to complement the half-pegs 44, 45, with the result that each half-peg enters the cavity 46, 47 when the pin stubs are pushed together (for the installation position, as illustrated in FIG. 3b). In the spread position, the half-pegs 44, 45 move out of the cavities 46, 47, said half-pegs being securely guided by the wide separating plane 49. Owing to this wide guidance in a flat plane, the spreading process does not lead to jamming or to tilting; the same applies when said half-pins are pushed together in the case of adjustment of the knee joint prosthesis. The design of the pin stubs 42, 43 is illustrated in detail in FIG. 4. Said pin stubs further have an actuator opening 48, which is designed to receive a spreading instrument 5, on their casing. Two actuator openings 48 are preferably provided for each pin stub, specifically symmetrically in relation to the separating plane 49. One is used in each case, specifically depending on the installation position. In the illustrated exemplary embodiment, the pin stubs 42, 43 are the same shape, that is to say the same element can be used both as pin stub 42 and also as pin stub 43.

In order to spread the pin stubs 42, 43, two access slots 38 are formed on the receiving eye 33. Said access slots are oriented on an aligned line with an orientation of their elongate extent in the direction of the center axis of the axial pin 4. A fastening opening 39 is provided above and centrally between said access slots. A pointed instrument can be inserted through the access slots 38, said instrument engaging in one of the two actuator openings 48. The pin stub 42 is removed from the other pin stub, and vice versa, by moving the instrument outward.

Figure 5:
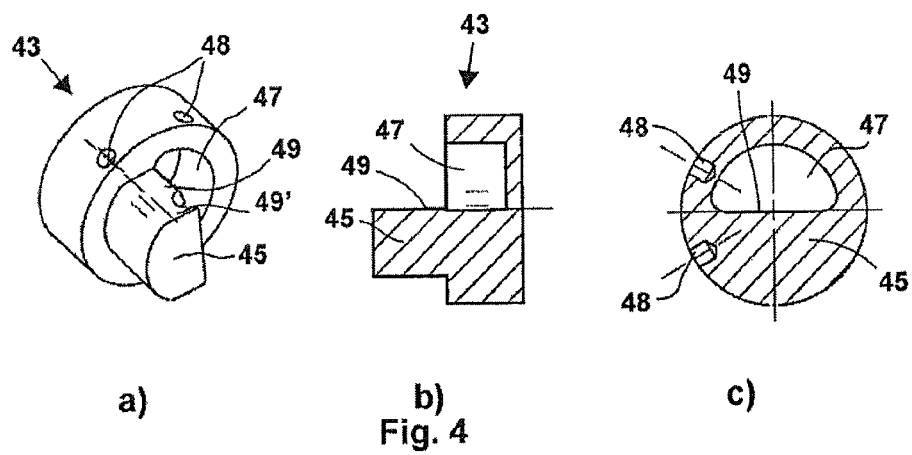
FIG. 5 shows a plan view of a spreading instrument.
Figure 6:
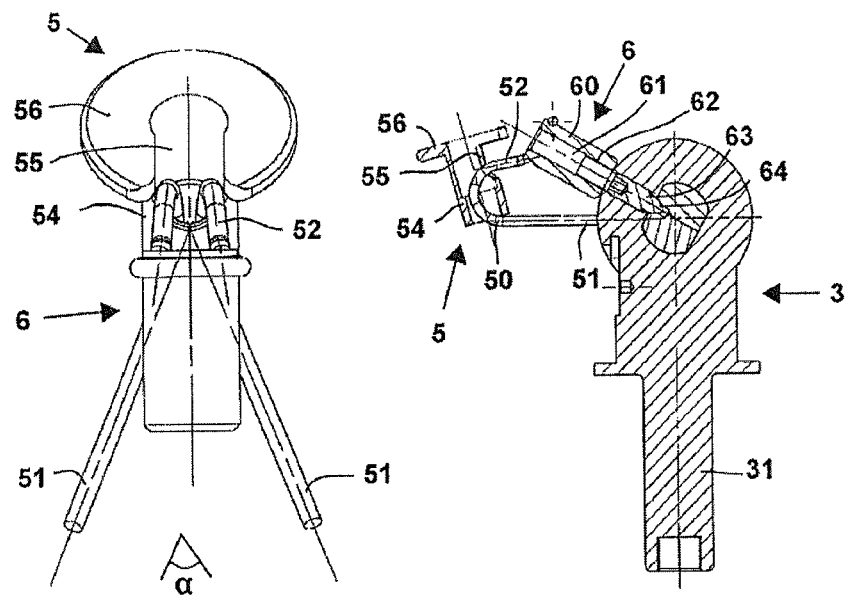
FIG. 6 shows a side view of the coupling piece with the spreading instrument in section.

The spreading instrument used for this purpose is illustrated in greater detail in FIGS. 5 and 6. Said spreading instrument comprises a wire clip 50 with two free ends 51 at its front end, said free ends diverging at an angle α. Said wire clip forms a three-point loop in its rear region, a sliding sleeve 54 being mounted on said three-point loop. Said sliding sleeve has a radially projecting collar 56, which is provided with a recess 55, on its side which faces away from the ends 51. The sliding sleeve 54 can, between its spreading position, as illustrated in FIG. 5, be moved forward into an inoperative position, as a result of which the free ends 51 are pushed into a position in which they are closer together. A certain adjustment force is required for this purpose, with the result that the sliding sleeve 54 functions as a means for preventing unintentional movement. The recess 55 ensures that the collar 56 does not collide with the wire clip 50 during the movement. Said recess also ensures unimpeded straight access to the fastening sleeve 60.

The fastening sleeve 60 is part of a fastening guide 6 which is arranged at the end of the wire clip 50. The fastening sleeve has an internal thread 62 in its inner opening 61, a locking screw 63 being screwed into said internal thread. In the inoperative position, the locking screw 63 projects only slightly by way of its tip 64, specifically to such an extent that it engages in the opening 39 by way of its thread and in this way secures the fastening guide to the coupling piece 3.

Figure 7:
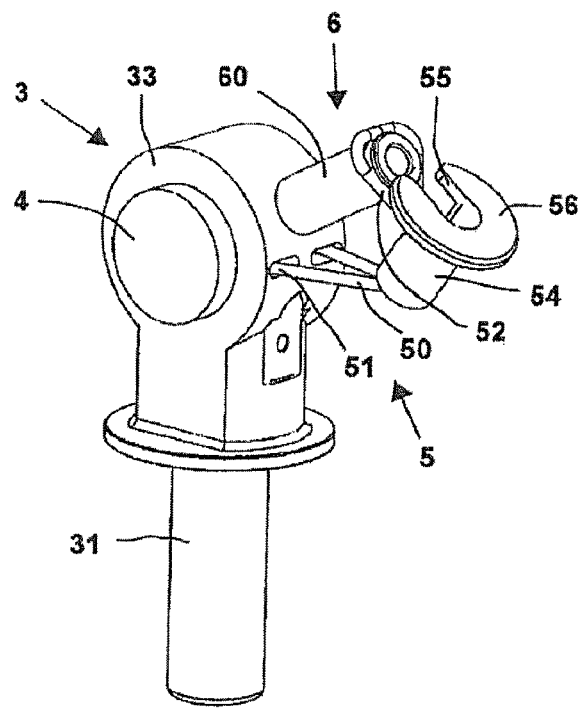
FIG. 7 shows a perspective view relating to FIG. 6.

During installation, the sliding sleeve 5 is moved backwards for the purpose of spreading the axial pin 4, as a result of which the free ends 51, which are inserted into the actuator openings 48 in the pin stubs 42, 43 through the access slots 38, are moved away from one another and thereby spread apart the pin stubs 42, 43. Once said pin stubs have reached their spread position (see FIGS. 3c and 7), the locking screw 63 is turned further, until it enters the separating plane 49 by way of its tip and secures the pin stubs 42, 43 by clamping and, if there is a corresponding receiving opening 49', even in an interlocking manner. If the locking screw 63 has been turned sufficiently far, it is no longer in engagement with the internal thread 62. The fastening guide 6 is therefore free, and the spreading instrument 5 can then be removed (for the first time). This ensures that the spreading instrument can be removed only when the pin stubs 42, 43 are spread.

Figure 8:
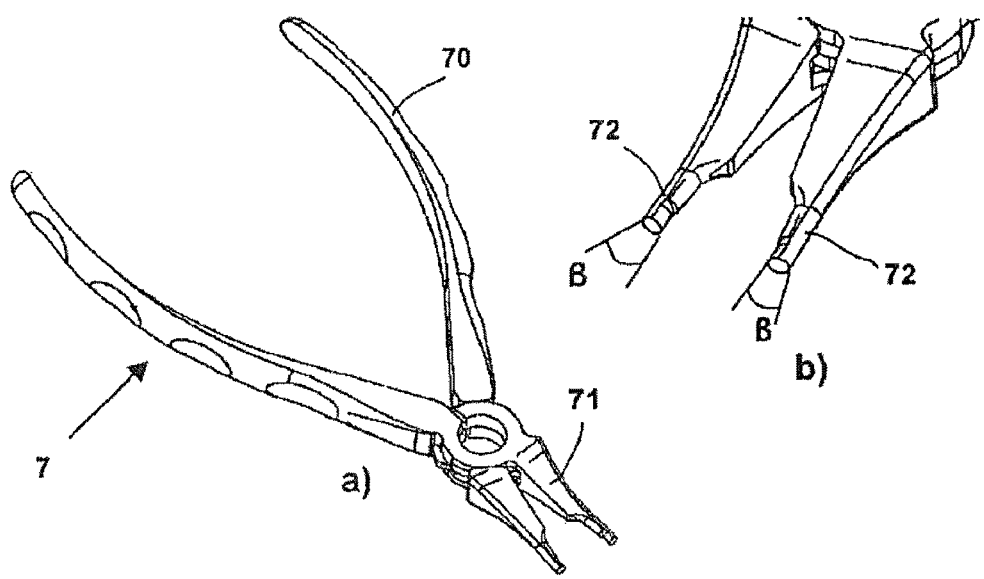
FIGS. 8a and b show a perspective view of a pair of adjustment pliers and a view of a detail of a pair of adjustment pliers.

In the event of an adjustment, it is necessary to move the pin stubs 42, 43 out of the spread position (see FIG. 3c) back into the installation position (see FIG. 3b). To this end, a set of adjustment pliers 7 is provided with a handle 70 at the rear end and with receiving fingers 70 on jaws 71 at the front end (see FIG. 8). The dimensions of the receiving fingers are such that said receiving fingers can be inserted through the access slots 38 and engage with the actuator openings 48. The receiving fingers 72 are preferably arranged in a converging manner. This means that they are oriented so as to point toward one another, specifically through an angle β of approximately 10 degrees. This angle is selected such that the receiving fingers 72 are approximately parallel in the position of the set of adjustment pliers 7 when the pin stubs 42, 43 have reached their installation position (see FIG. 3b), for the purpose of simpler removal.

The invention claimed is:

1. A joint prosthesis comprising a bending hinge formed by a hinge fork and an axial pin, the axial pin comprising two pin stubs arranged in an installation position, in which the pin stubs are retracted in a coupling piece for insertion purposes, and in an expanded position after implantation by being moved in an axial direction into aligned hinge holes in the hinge fork, wherein the axial pin has two bearing regions at its ends and a joining region situated between the bearing regions, and the axial pin is separated in the joining region such that a planar interface between the pin stubs is coplanar with a plane running along the axial direction and intersecting a circumferential surface of the axial pin at two locations.

2. The joint prosthesis of claim 1, wherein the plane is a central plane of the axial pin.

3. The joint prosthesis of claim 1, wherein the interface between the pin stubs is coplanar with a plurality of planes.

4. The joint prosthesis of claim 1, wherein the pin stubs have the same shape.

5. The joint prosthesis of claim 1, wherein the joining region of the pin stubs comprise half-pegs.

6. The joint prosthesis of claim 1, wherein the pin stubs have a half-moon shape in cross section.

7. The joint prosthesis of claim 1, wherein the coupling piece comprises a separating element configured to receive the joining region, the separating element having a non-round aperture for the pin stubs.

8. The joint prosthesis of claim 1, wherein a receiving element for a movement-prevention element of the pin stubs is formed on the coupling piece.

9. A joint prosthesis system comprising a joint prosthesis and a spreading instrument, wherein the joint prosthesis comprises a bending hinge formed by a hinge fork and an axial pin, the axial pin comprising two pin stubs arranged in an installation position, in which the pin stubs are retracted in a coupling piece for insertion purposes, and in an expanded position after implantation by being moved in an axial direction into aligned hinge holes in the hinge fork, wherein the axial pin has two bearing regions at its ends and a joining region situated between the bearing regions, and the axial pin is separated in the joining region such that a planar interface between the pin stubs is coplanar with a plane running along the axial direction and intersecting a circumferential surface of the axial pin at two locations, wherein an access slot is formed on the coupling piece for each pin stub, and wherein the spreading instrument is configured to engage in the pin stubs through the access slots.

10. The joint prosthesis system of claim 9, wherein the spreading instrument has a wire clip, the free ends of the wire clip being insertable into the access slots.

11. The joint prosthesis system of claim 10, wherein the free ends are arranged at an angle of 30 degrees to 70 degrees in relation to one another.

12. The joint prosthesis system of claim 10, wherein the wire clip forms, in its rear region which faces away from the ends, a loop in the opposite direction.

13. The joint prosthesis system of claim 9, comprising a sliding sleeve being movable from an inoperative position, in which the free ends are close to one another, to a spreading position in which the free ends are moved away from one another.

14. The joint prosthesis system of claim 13, wherein the spreading instrument has a fastening guide.

15. The joint prosthesis system of claim 14, wherein a thread is arranged on the fastening guide, a locking screw being screwed into said thread.

16. The joint prosthesis system of claim 15, wherein the length of the locking screw is greater than the distance between the fastening guide and the axial pin.

17. The joint prosthesis system of claim 13, wherein the sliding sleeve has a circumferential radial collar which has a recess on its side which faces the fastening guide.

18. The joint prosthesis system of claim 9 comprising a pair of adjustment pliers having handles at its rear end and receiving fingers at its front end, the receiving fingers being insertable into the access slots and having an oval cross section.

\* \* \* \* \*